US012661101B2

(12) United States Patent
Ozaki

(10) Patent No.: US 12,661,101 B2
(45) Date of Patent: Jun. 23, 2026

(54) RETRACTOR AND HOLDER

(71) Applicant: Shigeyuki Ozaki, Tokyo (JP)

(72) Inventor: Shigeyuki Ozaki, Tokyo (JP)

( * ) Notice: Subject to any disclaimer, the term of this patent is extended or adjusted under 35 U.S.C. 154(b) by 265 days.

(21) Appl. No.: 18/283,351

(22) PCT Filed: Mar. 15, 2022

(86) PCT No.: PCT/JP2022/011617
§ 371 (c)(1),
(2) Date: Sep. 21, 2023

(87) PCT Pub. No.: WO2022/202490
PCT Pub. Date: Sep. 29, 2022

(65) Prior Publication Data
US 2024/0164764 A1 May 23, 2024

(30) Foreign Application Priority Data

Mar. 23, 2021 (JP) ................................. 2021-048684
Jul. 21, 2021 (JP) ................................. 2021-120837

(51) Int. Cl.
*A61B 17/02* (2006.01)
*A61B 17/00* (2006.01)
(Continued)

(52) U.S. Cl.
CPC .............................. *A61B 17/0218* (2013.01);
*A61B 2017/00473* (2013.01); *A61B 2017/00783* (2013.01);
(Continued)

(58) Field of Classification Search
CPC ..... A61B 17/02; A61B 17/0218; A61B 17/00; A61B 17/04; A61B 17/22; A61B 17/0293; A61B 90/02
See application file for complete search history.

(56) References Cited

U.S. PATENT DOCUMENTS

| | | | |
|---|---|---|---|
| 6,017,304 A | 1/2000 | Vierra et al. | |
| 2002/0092533 A1 | 7/2002 | Boyd et al. | |

(Continued)

FOREIGN PATENT DOCUMENTS

| | | |
|---|---|---|
| CN | 201500148 U | 6/2010 |
| JP | 60-501543 A | 9/1985 |

(Continued)

OTHER PUBLICATIONS

Japanese Notice of Reasons for Refusal for 2021-120837, dated Aug. 31, 2021.

(Continued)

*Primary Examiner* — Christopher J Beccia
(74) *Attorney, Agent, or Firm* — Sughrue Mion, PLLC

(57) ABSTRACT

A retractor includes plural holes penetrating from a front surface to a back surface of the retractor. The retractor is inserted into an aorta. When one end side of a thread that penetrates from the front surface to the back surface through one of the holes and penetrates from an inside to an outside of the aorta, and the other end side of the thread that penetrates from the front surface to the back surface through a hole of the plural holes different from the hole through which the one end side penetrates and penetrates from the inside to the outside of the aorta are pulled, the aorta is widened in a radial direction.

7 Claims, 10 Drawing Sheets

(51) Int. Cl.

| | | |
|---|---|---|
| *A61B 17/04* | (2006.01) | |
| *A61B 17/22* | (2006.01) | |

(52) U.S. Cl.

CPC ................. *A61B 2017/0414* (2013.01); *A61B 2017/0464* (2013.01); *A61B 2017/22082* (2013.01)

(56)            References Cited

U.S. PATENT DOCUMENTS

| | | | | |
|---|---|---|---|---|
| 2003/0055318 | A1* | 3/2003 | Vierra ................ | A61B 17/0469 600/204 |
| 2011/0270307 | A1 | 11/2011 | Szabo et al. | |
| 2014/0316519 | A1* | 10/2014 | Veseley ................ | A61F 2/2427 623/2.11 |
| 2017/0035404 | A1 | 2/2017 | Foster et al. | |
| 2020/0060670 | A1 | 2/2020 | Chawla | |

FOREIGN PATENT DOCUMENTS

| | | | |
|---|---|---|---|
| JP | 2002-125976 | A | 5/2002 |
| WO | 01/80725 | A1 | 11/2001 |

OTHER PUBLICATIONS

Japanese Notice of Reasons for Refusal for 2021-176703, dated Dec. 21, 2021.

Japanese Notice of Reasons for Refusal for 2021-176703, dated May 10, 2021.

International Search Report for PCT/JP2022/011617, dated May 17, 2022.

Written Opinion for PCT/JP2022/011617, dated May 17, 2022.

European Search Report issued Jan. 5, 2024 in Application No. 22775280.5.

Communication issued May 19, 2025 in European Application No. 22775280.5.

Communication dated Mar. 23, 2026, in Chinese Application No. 202280033847.2.

* cited by examiner

RETRACTOR AND HOLDER

CROSS REFERENCE TO RELATED APPLICATIONS

This application is a National Stage of International Application No. PCT/JP2022/011617 filed Mar. 15, 2022, claiming priority based on Japanese Patent Application No. 2021-048684 filed Mar. 23, 2021 and Japanese Patent Application No. 2021-120837 filed Jul. 21, 2021, the contents of each of the International Application and the two Japanese Patent Applications being herein incorporated by reference in their entireties.

TECHNICAL FIELD

The present invention relates to a holder and a retractor.

BACKGROUND ART

As an instrument that supports a blood vessel, for example, there is a blood vessel support tool disclosed in Patent Document 1. In the blood vessel support tool, needle portions formed at tips of a pair of arm portions are used to pierce a blood vessel, and the arm portions are opened and closed, thereby widening an incision between the needle portions.

CITATION LIST

Patent Document

Patent Document 1: Japanese Patent Application Laid-Open No. 2002-125976

SUMMARY OF THE INVENTION

Problems to be Solved by the Invention

When performing aortic valvuloplasty, it is necessary to widen the aorta in a radial direction. The blood vessel support tool disclosed in Patent Document 1 is capable of expanding a portion of the blood vessel in which an incision has been made in a direction in which the blood vessel extends, but is not suitable for maintaining a state in which a cross section of the aorta is widened in the radial direction.

An object of the present invention is to maintain a state in which the aorta is widened in the radial direction.

Means for Solving the Problems

In one aspect of the present invention, there is provided a retractor having a plate shape, including a plurality of holes penetrating from a front surface to a back surface, in which the retractor is inserted into an aorta, and when one end side of a thread that penetrates from the front surface to the back surface through one of the plurality of holes and penetrates from an inside to an outside of the aorta, and the other end side of the thread that penetrates from the front surface to the back surface through one of the plurality of holes different from the hole through which the one end side penetrates, and that penetrates from the inside to the outside of the aorta are pulled, the aorta is widened in a radial direction.

In a preferred aspect, the retractor is used for aortic valvuloplasty, which is inserted into a region in the aorta including a valsalva sinus.

In a preferred aspect, a center portion in a lateral direction is curved so as to be recessed.

In a preferred aspect, the plurality of holes includes a plurality of first holes that penetrate from the front surface to the back surface and through which the thread passes, and a second hole whose diameter is larger than a diameter of each of the plurality of first holes and which is for injecting a myocardial protective liquid.

In a preferred aspect, the plate-shaped member has a portion configured to be warped in a direction opposite to a recessed direction toward one end in a longitudinal direction.

In a preferred aspect, the retractor further includes a passage formed inside to suck blood, a hole for taking the blood into the passage, and a connecting portion for connecting a tube configured to be connected to the passage, protruding from a side surface of the plate-shaped member, and sucking the blood into the passage.

In a preferred aspect, the retractor further includes a third hole through which the thread passes for pulling the retractor from outside a chest wall.

In a preferred aspect, one end portion in a longitudinal direction has a hook shape.

In a preferred aspect, the retractor further includes a hole through the thread passes for pulling the retractor from outside the chest wall.

A tip portion of the retractor may have a hook shape.

The retractor may further include a grip portion.

The present invention provides a holder including an annular portion that has an annular shape and is formed of a plurality of notches on an upper surface in a radial direction; and a support portion that supports the annular portion, in which the holder is disposed such that an aorta is located inside an inner periphery of the annular portion, and a thread configured to be hooked on a retractor disposed in the aorta and to penetrate from an inner wall side to an outer wall side of the aorta is fixed by the notch.

In a preferred aspect, the plurality of notches is formed at predetermined intervals in a circumferential direction.

In a preferred aspect, the annular portion is configured to be attachable to and detachable from the support portion.

In a preferred aspect, the annular portion has an arc shape.

Advantageous Effect of the Invention

According to the present invention, it is possible to maintain a state in which the aorta is widened in the radial direction.

MODE FOR CARRYING OUT HE INVENTION

[Embodiments]

Figure 1:
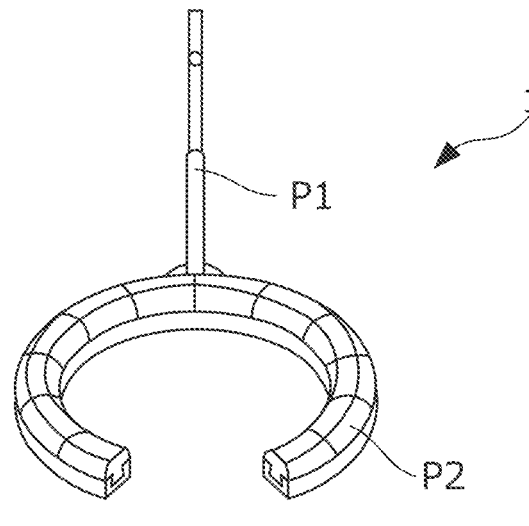
FIG. 1 is a perspective view of a holder 1 according to an embodiment of the present invention.
Figure 2:
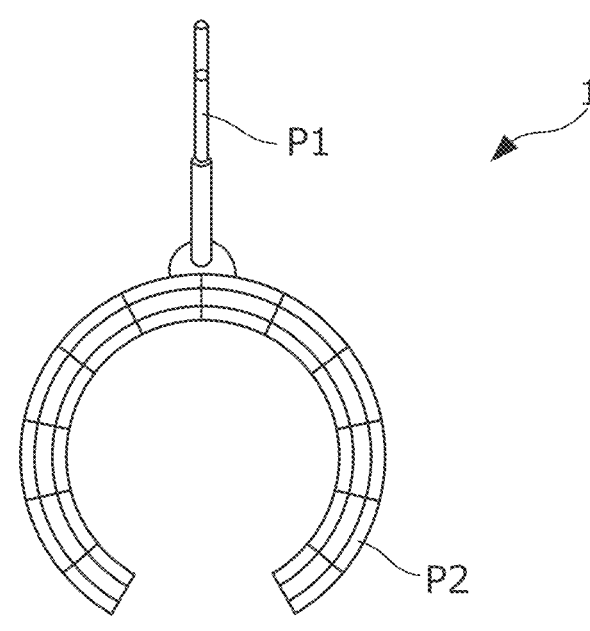
FIG. 2 is a top view of the holder 1.
Figure 3:
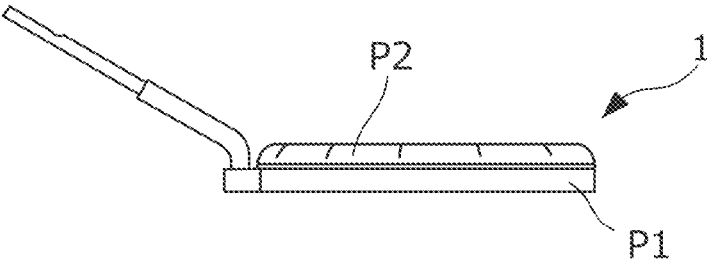
FIG. 3 is a side view of the holder 1.

FIG. 1 is a perspective view of a holder 1 according to an embodiment of the present invention, FIG. is a top view of the holder 1, and FIG. 3 is a side view of the holder 1. The holder 1 is a surgical instrument for widening the aorta in a radial direction in aortic valvuloplasty. The holder 1 according to the present embodiment is composed of a first component P1 and a second component P2.

Figure 4:
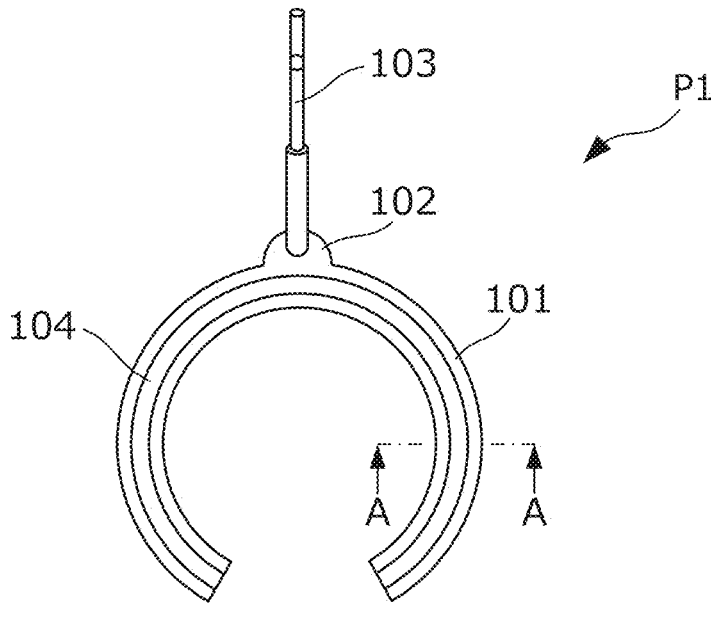
FIG. 4 is a top view of a first component P1.
Figure 5:
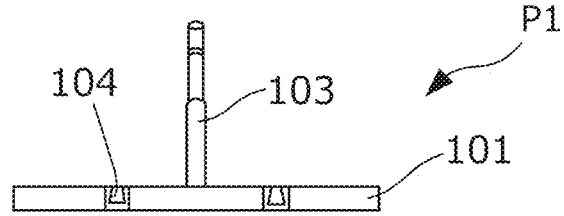
FIG. 5 is a front view of the first component P1.
Figure 6:
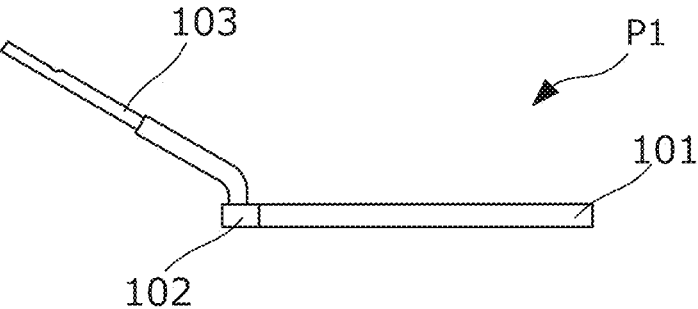
FIG. 6 is a side view of the first component P1.
Figure 7:
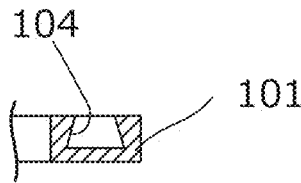
FIG. 7 is a sectional view taken along line A-A of FIG. 4.

FIG. 4 is a top view of the first component P1, FIG. 5 is a front view of the first component P1, FIG. 6 is a side view of the first component P1, and FIG. 7 is a sectional view taken along line A-A of FIG. 4. A material of the first component P1 according to the present embodiment is, for example, a metal material suitable for a surgical instrument. The material of the first component 1 is not limited to a metal material, and may be, for example, a synthetic resin.

The first component P1 is composed of an annular portion 101, which is annular when viewed from above, a base portion 102, which is semicircular when viewed from above, and a shaft portion 103, which extends upward from the base portion 102. The annular portion 101 has an arc shape when viewed from above and a groove 104 is formed on an upper surface side. In the present embodiment, an inner diameter of the annular portion 101 is 60 mm and an outer diameter of the annular portion 101 is 80 mm, but the inner diameter and the outer diameter are not limited to these dimensions, and may be other dimensions. In addition, a central angle of the arc shape is 300° in the annular portion 101, but the central angle is not limited to this angle and may be another central angle. A thickness of the annular portion 101 in a vertical direction is 5 mm in the present embodiment, but may be less than 5 mm or more than 5 mm annular portion 101 in the radial direction is 10 mm in the present embodiment, but the width may be less than 10 mm or more than 10 mm.

The groove 104 reaches from one end to the other end of the annular portion 101 along the circumferential direction of the annular portion 101, and a cross section thereof has a trapezoidal shape. The base portion 102 is formed on an outer peripheral surface side of the annular portion 101 and is formed in a semicircular shape when viewed from above.

The shaft portion 103 is a cylindrical shaft formed upward at a predetermined angle with respect to the upper surface of the base portion 102.

Figure 8:
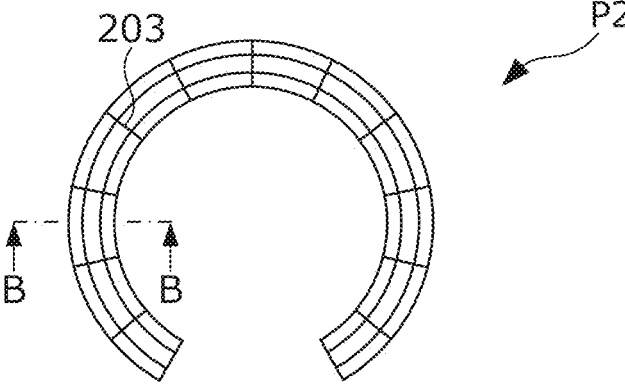
FIG. 8 is a top view of a second component P2.
Figure 9:
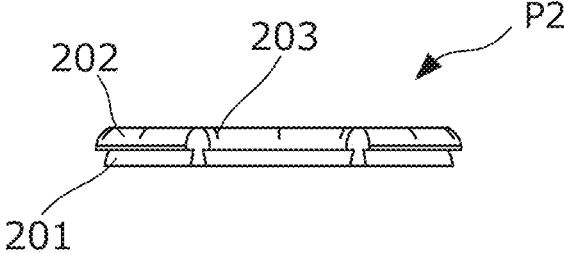
FIG. 9 is a front view of the second component P2.
Figure 10:
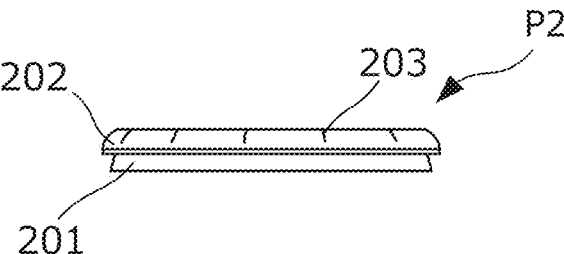
FIG. 10 is a side view of the second component P2.
Figure 11:
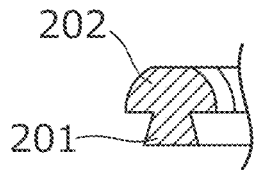
FIG. 11 is a sectional view taken along line B-B of FIG. 8.

FIG. 8 is a top view of the second component P2, FIG. 9 is a front view of the second component P2, FIG. 10 is a side view of the second component P2, and FIG. 11 is a sectional view taken along line B-B of FIG. 8. A material of the second component P2 according to the present embodiment is a synthetic resin having elasticity. The material of the second component P2 is not limited to the synthetic resin and may be, for example, rubber. In addition, the material of the second component P2 may be an adhesive material.

The second component P2 has an arc shape when viewed from above, has a trapezoidal cross section, and has a lower portion 201, which fits into the groove 104, and an upper portion 202, which is formed on the tower portion 201 and in which a plurality of notches 203 is formed in the radial direction. In the present embodiment, an inner diameter of the second component P2 is 60 mm and an outer diameter of the second component P2 is 80 mm, but the inner diameter and the outer diameter are not limited to these dimensions, and may have other dimensions. In addition, a central angle of the arc shape is 300° in the second component P2, but the central angle is not limited to this angle and may be another central angle. A thickness of the second component P2 in the vertical direction is 8.6 mm in the present embodiment, but may be less than 8.6 mm or more than 8.6 mm. A width of the second component P2 in the radial direction is 10 mm in the present embodiment, but the width may be less than 10 mm or more than 10 mm. A portion of a curved surface of the upper portion 202 is a curved surface having a radius of 5 min and a width of a flat portion on the upper surface in the radial direction is 4 mm. These dimensions of the second component P2 are examples and may be other dimensions.

The plurality of notches 203 has a predetermined depth from the front surface of the upper portion 202, and clamp and fix threads used for surgery. A width of the notch 203 in the circumferential direction is 0.2 mm, but is not limited to 0.2 mm, and may be another dimension. Further, in the present embodiment, an angle formed by a virtual line drawn to the center from the notch 203 closest to one end and a virtual line drawn to the center from the notch 203 closest to the other end of the second component P2 in the circumferential direction is 100', and the other notches 203 form an angle of 26° between adjacent virtual lines when the virtual lines are drawn toward the center. The plurality of notches 203 is preferably formed at equal intervals in the circumferential direction, but may not be formed at equal intervals in the circumferential direction. In addition, the number of the plurality of notches 203 is not limited to 11 illustrated in the drawing, and may be more or less than 11.

The second component P2 is held by the first component P1 by fitting the lower portion 201 into the groove 104. In the holder 1 configured of the first component P1 and the second component P2, the annular portion 101 and the second component P2 are examples of the annular portion according to the present invention, and the base portion 102 and the shaft portion 103 are examples of the support portion according to the present invention.

Figure 12:
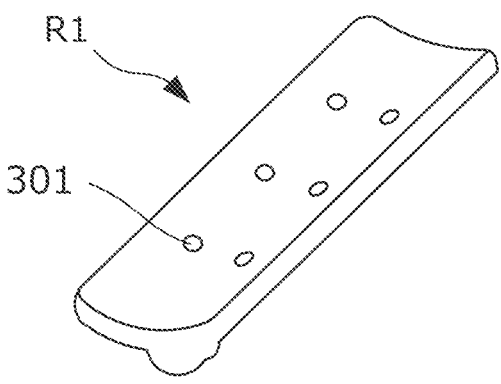
FIG. 12 is a perspective view of a retractor R1.
Figure 13:
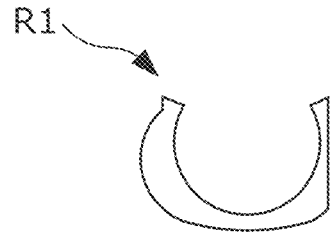
FIG. 13 is a front view of the retractor R1.
Figure 14:
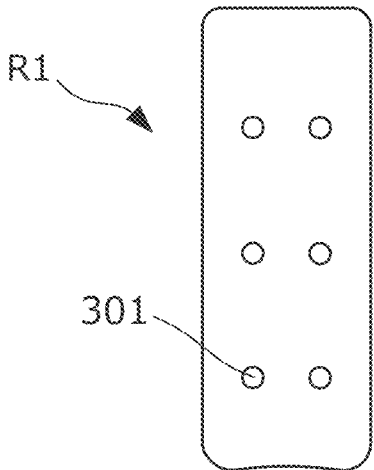
FIG. 14 is a top view of the retractor R1.
Figure 15:
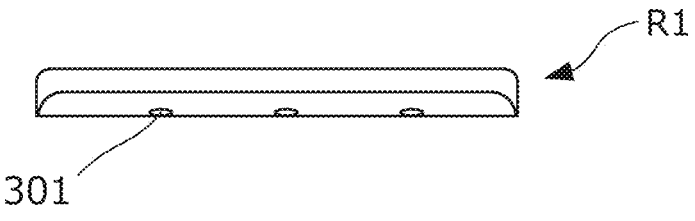
FIG. 15 is a side view of the retractor R1.

FIG. 12 is a perspective view of a retractor R1 according to an embodiment of the present invention, FIG. 13 is a front view of the retractor R1, FIG. 14 is a top view of the retractor R1, and FIG. 15 is a side view of the retractor R1. A material of the retractor R1 is, for example, a metal material suitable for the surgical instrument. The material of the retractor R1 is not limited to a metal material and may be, for example, a synthetic resin.

The retractor R1 is inserted into a region in the aorta including, for example, the valsalva sinus. The retractor R1 has a plate shape having a longitudinal direction and a lateral direction and, as illustrated in FIG. 13, a center portion in the lateral direction is curved so as to be recessed. In the retractor R1, a plurality of holes 301 that penetrates from the front surface to the back surface are formed in a matrix. In the illustrated retractor R1, the number of the holes 301 is 6, but may be more or less than 6. In addition, in the illustrated retractor R1, the holes 301 are formed in 3 rows and 2 columns, but may be disposed in another matrix as long as there are 2 columns or more.

Figure 16:
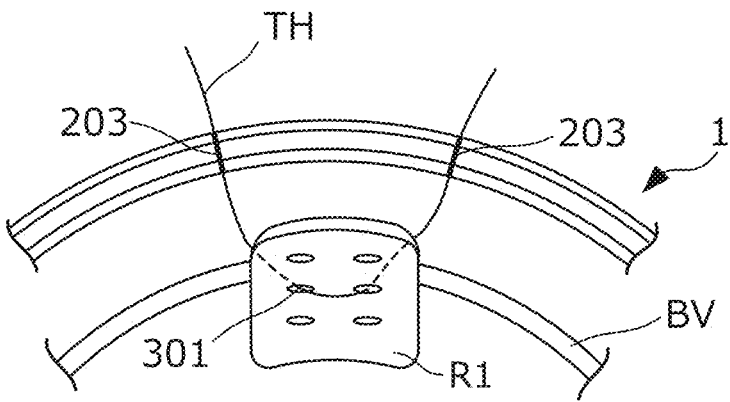
FIG. 16 is a schematic view of a cut ascending aorta BV as viewed from above.
Figure 17:
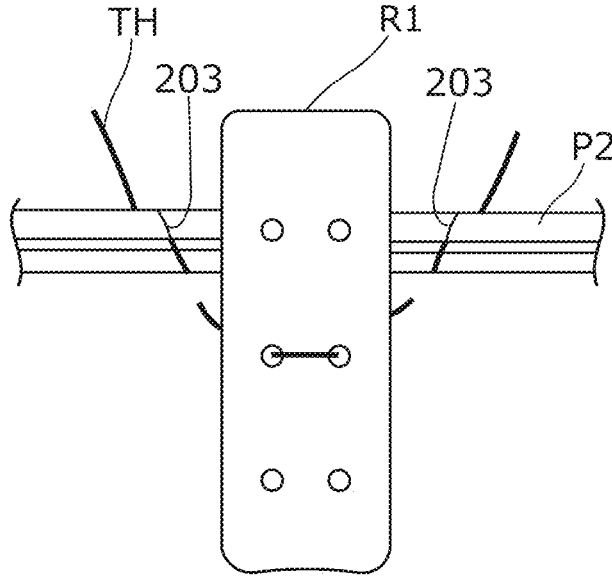
FIG. 17 is a schematic view of the cut ascending aorta BV as viewed from an inner wall side.
Figure 18:
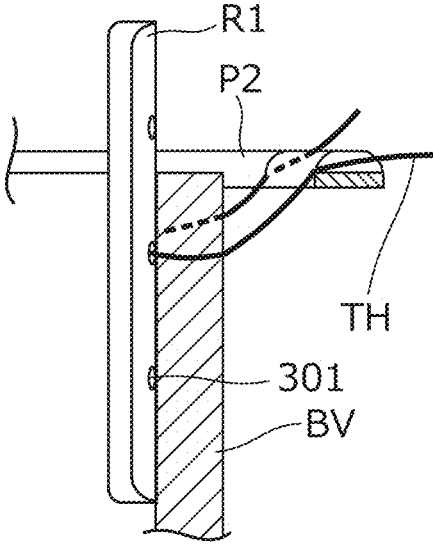
FIG. 18 is a schematic sectional view of the ascending aorta BV cut an extending direction of the ascending aorta BV.

Next, a method of using the holder 1 and the retractor R1 will be described with reference to FIGS. 16 to 18. FIG. 16 is a schematic view of a cut ascending aorta. BV as viewed from above. FIG. 17 is a schematic view of the cut ascending aorta BV as viewed from an inner wall side. FIG. 18 is a schematic sectional view of the ascending aorta BV cut in an extending direction of the ascending aorta BV.

As illustrated in FIG. 16, an operator disposes the holder 1 such that the cut ascending aorta. BV is located inside an inner periphery of the second component P2 of the holder 1, and fixes the shaft portion 103 with a flexible arm. The shaft portion 103 is preferably located on the back side thereof, not on the front side as viewed by the operator.

Next, as illustrated in FIGS. 16 and 17, the operator allows a surgical thread TH to pass through two holes 301 arranged on the left and right sides from the front surface side of the retractor R1. As illustrated in FIG. 18, the operator causes the thread TH protruding to the back side to penetrate from the inner wall side to the outer wall side of the ascending aorta BV with a surgical needle, and pulls the thread TH that penetrates the outer wall side of the ascending aorta BV. Since the thread TH is hung on the front surface of the retractor R1, the retractor R1 comes into contact with the inner wall of the ascending aorta BV when the operator pulls the thread TH. When the thread TH is further pulled toward the holder 1 side in the state illustrated in FIG. 18, the retractor R1 pulled by the thread TH widens the ascending aorta BV in the radial direction. In a state in which the ascending aorta BV is widened in the radial direction, the operator inserts the pulled thread TH into the notch 203 of the second component P2 to fax the thread TH. The operator widens the ascending aorta BV in the radial direction as described above with the plurality of retractors R1.

According to the present embodiment, the operator is able to widen the aorta in the radial direction without the help of an assistant. In addition, according to the present embodiment, since the holder 1 is fixed by one flexible arm, it is possible to widen a surgical field as compared with a case in which the aorta is widened in the radial direction by attachments mounted on the tips of the plurality of flexible arms.

[Modified Examples]

Although the embodiments of the present invention have been described above, the present invention is not limited to the above-described embodiments, and is able to be implemented in various other forms. For example, the present invention may be implemented by modifying the above-described embodiment as described below. In addition, the above-described embodiment and the following modified examples may be used in combination.

Figure 19:
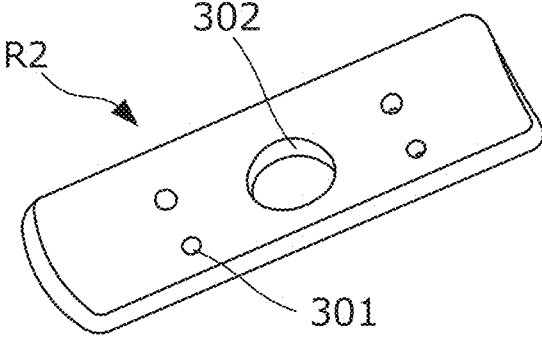
FIG. 19 is a perspective view of a retractor R2.
Figure 20:
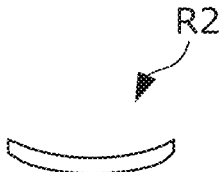
FIG. 20 is a front view of the retractor R2.
Figure 21:
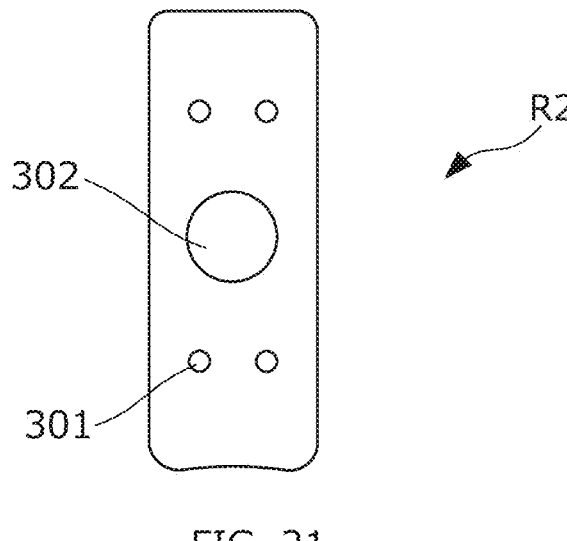
FIG. 21 is a top view of the retractor R2.
Figure 22:
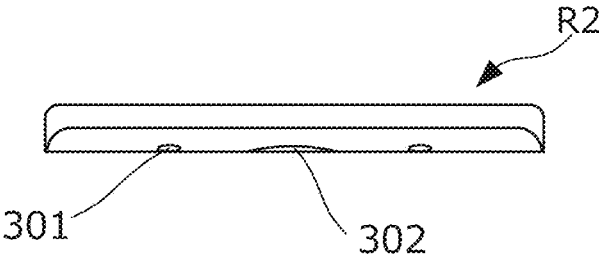
FIG. 22 is a side view of the retractor R2.

In the above-described embodiments, the retractor R1 has a matrix of holes 301 having the same shape, but the configuration of the holes formed in the retractor R1 is not limited to the configuration of the embodiments. FIG. 19 is a perspective view of a retractor R2 according to a modified example of the present invention. FIG. 20 is a front view of the retractor R2, FIG. 21 is a top view of the retractor R2, and FIG. 22 is a side view of the retractor R2. A material of the retractor R2 is, for example, a metal material suitable for the surgical instrument. The material of the retractor R2 is not limited to the metal material, and may be, for example, a synthetic resin. In the retractor R2, holes 301 are formed in 2 rows and 2 columns, and a hole 302 is formed between the hole 301 in the first row and the hole 301 in the second row. The hole 302 may be formed in one row instead of 2 rows.

When being inserted into the aorta, the retractor R2 is inserted such that the hole 302 is located at a position of the coronal ostium of the aorta. Since the hole 302 penetrates from the front surface to the back surface, a cannula for injecting the myocardial protective liquid is inserted into the coronal ostium from the front surface of the retractor R2 through the hole 302, and the myocardial protective liquid R2 is able to be injected into the coronary ostium without removal of the retractor R2.

The retractor R1 and the retractor R2 may be transparent materials when the material is the synthetic resin.

In the above-described embodiments, the holder 1 is configured of the first component P1 and the second component P2, but it may have a configuration in which the material of the first component P1 is the synthetic resin, and the upper portion 202 is integrally molded on the annular portion 101.

In the above-described embodiments, the annular portion 101 and the second component P2 have the arc shape when viewed from above, but may have an annular shape. In addition, the annular portion 101 and the second component P2 may have an annular polygonal shape or an annular elliptical shape when viewed from above.

Figure 23:
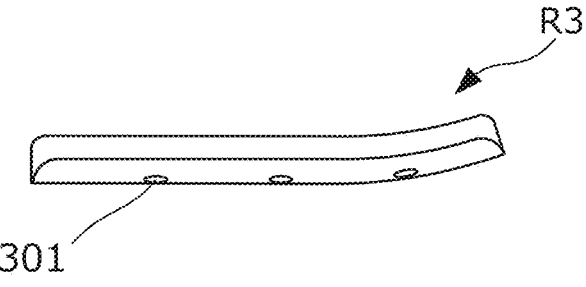
FIG. 23 is a side view of a retractor R3.

FIG. 23 is a side view of a retractor R3 according to a modified example of the present invention. The retractor R3 has a shape in which one end of the retractor R1 is warped toward the upper surface side. That is, the retractor R3 has a portion configured to be warped in a direction opposite to the recessed direction toward one end in the longitudinal direction. According to the retractor R3, a back surface side of a bent portion of the retractor R3 is in contact with a curved surface portion of an inner wall of a valsalva sinus, and the back surface side of the retractor R3 is in close contact with the inner wall of the valsalva sinus to widen the aorta.

Figure 24:
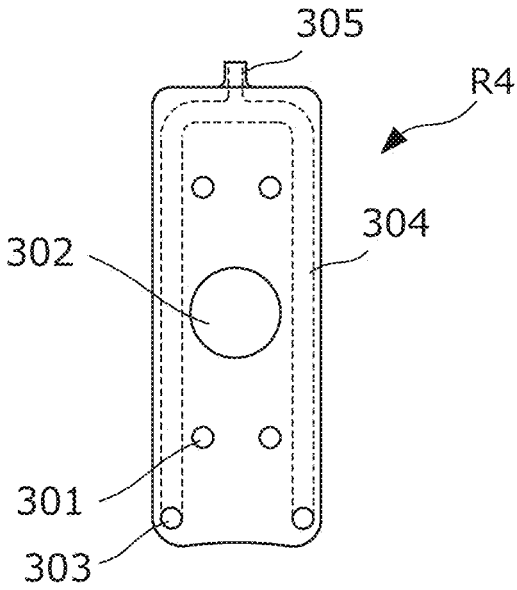
FIG. 24 is a bottom view of a retractor R4.

The retractor R2 may have a configuration in which a passage for sucking blood from the coronary arteries is provided inside thereof. FIG. 24 is a bottom view of a retractor R4 according to a modified example. The retractor R4 has, in addition to the holes 301 and the hole 302, a hole 303, a passage 304, and a connecting portion 305. The hole 303 is a hole provided on the lower surface side. In the illustrated retractor R4, the hole 303 does not penetrate the retractor R4, but the hole 303 may penetrate the retractor R4. The passage 304 is a passage provided inside the retractor R4 and leads to the hole 303. The connecting portion 305 is hollow and protrudes from the side surface of the retractor R4, and the hollow portion is open to the outside. In addition, the connecting portion 305 has a circular cross section and the hollow portion leads to the passage 304. The retractor R4 is disposed such that the hole 303 is located below the hole 302 and below the coronal ostium when being located in the aorta. In addition, a tube for performing suction is connected to the connecting portion 305. During the surgery of aortic valvuloplasty, blood in the coronary artery may flow out into the valsalva sinus. When the retractor R4 is used, the blood that has flowed into the valsalva sinus is sucked into the passage 304 from the hole 303, and is able to be sucked out of the aorta through the passage 304 and the connecting portion 305.

Figure 25A:
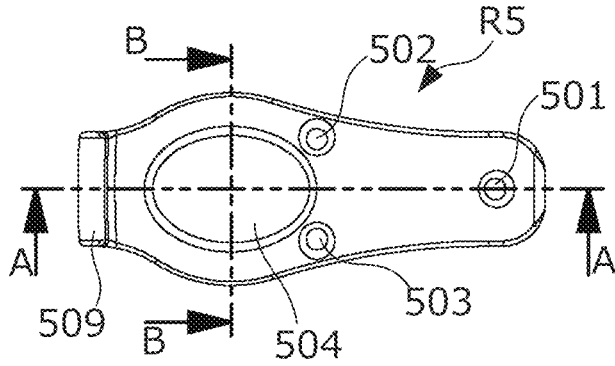
FIG. 25A is a view illustrating a retractor R5.
Figure 25B:
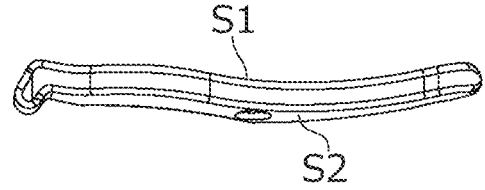
FIG. 25B is a view illustrating the retractor R5.
Figure 25C:
FIG. 25C is a view illustrating the retractor R5.
Figure 25D:
FIG. 25D is a view illustrating the retractor R5.
Figure 25E:
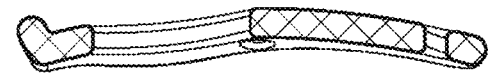
FIG. 25E is a view illustrating the retractor R5.

FIGS. 25A to 25E are views of a retractor R5 according to another modified example of the present invention. FIG. 25A is a plan view, FIG. 25B is a side view, FIG. 25C is a right side view, FIG. 25D is a sectional view along the B-B line, and FIG. 25E is a sectional view along A-A line. The retractor R5 has a plate shape having S1 and S2, is slightly warped in a plan view, and has a shape in which the center is slightly bulged in a right side view. A tip portion 509 has a hook (folded back) shape for being hooked on an inner wall of the aorta or other target site and fixing the retractor R5. The retractor R5 has holes 501 to 504.

Specifically, the thread passes through the hole 501 formed in a rear end portion, is taken directly out to the chest wall, and is pulled (lifted) from the outside of the chest wall by a predetermined method to secure a field of view of the aortic valve while expanding the aortic valve in the radial direction. The holes 502 and 503 are holes for the thread with a pledget to pass through. The retractor R5 is fixed to the aorta by penetrating the thread from the inner wall to an outer wall of the ascending aorta BV. The hole 504 is for injecting the myocardial protective liquid directly from the right coronary arteries in a state in which the retractor R5 is disposed. Accordingly, it is not necessary to remove the retractor R5 to inject the myocardial protective liquid.

The operator inserts the retractor R5 into the body from the tip portion 509, hooks the tip portion 509 to a desired location to fix the retractor R5 to the inner wall of the aorta, and pulls the thread passing through the hole 501 from the outside of the chest wall to secure the field of view of the aortic valve while expanding the aortic valve in the radial direction. At this time, a slight bulge in the center portion in a side view fits the shape of the valsalva sinus.

It is preferable to use two or more retractors R5 at the same time.

In the retractors R1 to R5 described above, it is possible to adopt a usage method in which the thread passes through the holder and is fixed when the holder is able to be inserted into the body, such as in surgery with a median incision to open the sternum. On the other hand, in a lightly invasive heart surgery (for example, a cut of about 10 cm between the ribs), it is often the case that the holder 1 cannot be inserted into the body. In such a case, the retractors R1 to R5 may pull the thread applied to the retractor from the outside of the chest wall. Alternatively, the retractors R1 to R5 may be fixed to the pericardium that surrounds the retractors R1 to R5. In short, the retractors R1 to R5 may be used alone or as a set with the holder 1 and other fixing devices, and the fixing method thereof is not limited.

Figure 26A:
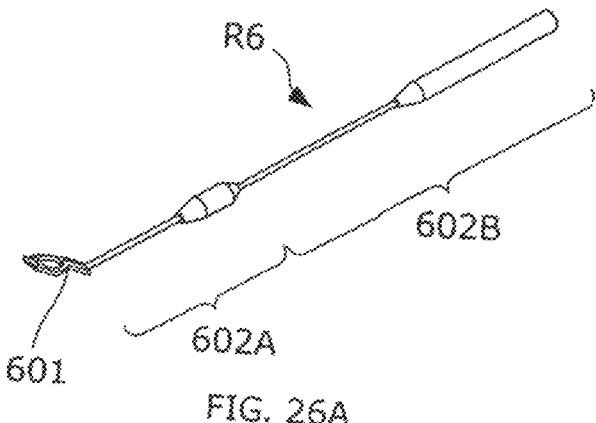
FIG. 26A is a view illustrating a retractor R6.
Figure 26B:
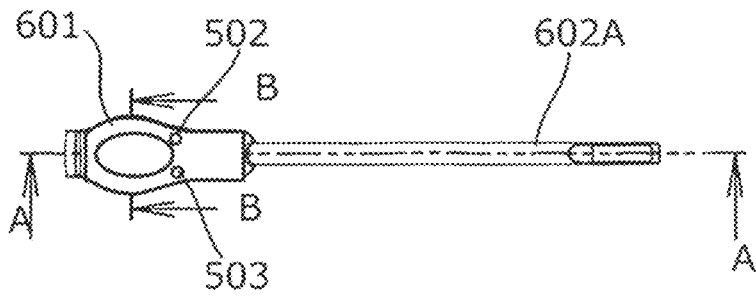
FIG. 26B is a view illustrating the retractor R6.
Figure 26C:
FIG. 26C is a view illustrating the retractor R6.
Figure 26D:
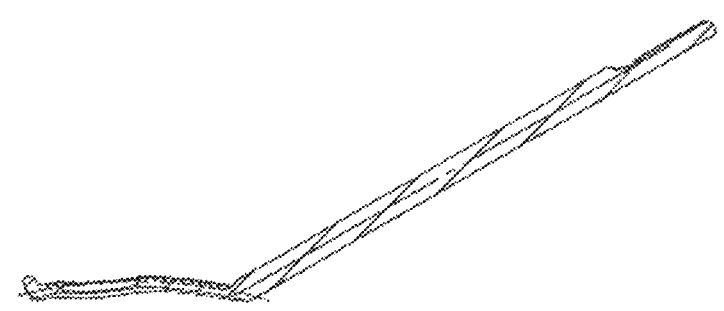
FIG. 26D is a view illustrating the retractor R6.

In each of the above-described retractors R1 to R5, a grip portion (handle) for an operator to hold may be provided. FIGS. 26A to 26D illustrate a retractor R6 according to another modified example of the present invention, FIG. 26A is an overall perspective view, FIG. 26B is an enlarged view of the tip portion, FIG. 26C is a sectional view of B-B, and FIG. 26D is a sectional view of A-A. The retractor R6 includes a body portion 601 in which the hole 504 is omitted from the retractor R5 illustrated in FIG. 25, a grip portion 602B of which a rear end is gripped by the operator, and a shaft portion 602A that connects the body portion 601 and the grip portion 602B. That is, according to the retractor R6, it is not necessary to use an instrument such as forceps. In addition, the operator is able to make up for the lack of fixing force due to the pledget. In addition, in R6, the holes 502 and 503 through which the pledget passes may be omitted.

DESCRIPTION OF REFERENCE NUMERALS 1 holder
101 annular portion
102 base portion
103 shaft portion
104 groove
201 lower portion
202 upper portion
203 notch
301 hole
307 hole
303 hole
304 passage
305 connecting portion
P1 first component
P2 second component
R1, R2, R3, R4, R5, R6 retractor
TH Thread
BV ascending aorta
501, 502, 503, 504 hole

The invention claimed is:
1. A retractor that is a plate-shaped member, the retractor comprising:
a plurality of holes penetrating from a front surface to a back surface,
wherein:
the retractor is configured to be inserted into an aorta,
when one end side of a thread that penetrates from the front surface to the back surface through one of the plurality of holes and is configured to penetrates from an inside to an outside of the aorta, and the other end side of the thread that penetrates from the front surface to the back surface through a hole of the plurality of holes different from the hole through which the one end side penetrates and is configured to penetrates from the inside to the outside of the aorta are pulled, the aorta is widened in a radial direction,
the plate-shaped member has a portion configured to be warped in a direction opposite to a recessed direction toward one end in a longitudinal direction, and
the plurality of holes includes a plurality of first holes that penetrates from the front surface to the back surface and through which the thread passes, and a second hole whose diameter is larger than a diameter of each of the plurality of first holes, is circular or oval in shape, and is configured to receive a cannula for injecting a myocardial protective liquid.
2. The retractor according to claim 1,
wherein the retractor is used for aortic valvuloplasty, and is configured to be inserted into a region in the aorta including a valsalva sinus.
3. The retractor according to claim 1,
wherein a center portion in a lateral direction of the retractor is curved so as to be recessed.
4. The retractor according to claim 1, further comprising:
a passage formed inside to suck blood;
a hole for taking the blood into the passage; and
a connecting portion for connecting a tube configured to be connected to the passage, protruding from a side surface of the plate-shaped member, and sucking the blood in the passage.

5. The retractor according to claim 1, further comprising:

a third hole through which the thread passes for pulling the retractor from an outside a chest wall.

6. The retractor according to claim 1, wherein one end portion of the retractor in a longitudinal direction has a hook shape.

7. The retractor according to claim 1, further comprising:

a grip portion.

* * * * *

5